United States Patent [19]
Heffelfinger et al.

[11] Patent Number: 6,043,506
[45] Date of Patent: Mar. 28, 2000

[54] MULTI PARAMETER SCANNER

[75] Inventors: David M. Heffelfinger, San Pablo;
Rebecca Ann Batterson, San Rafael;
Renato Salgado, Rodeo, all of Calif.

[73] Assignee: Bio-Rad Laboratories, Inc., Hercules, Calif.

[21] Appl. No.: 09/001,254

[22] Filed: Dec. 30, 1997

Related U.S. Application Data
[60] Provisional application No. 60/055,567, Aug. 13, 1997.

[51] Int. Cl.$^7$ .......................... G03B 42/02; G01N 21/64
[52] U.S. Cl. ..................................... 250/584; 250/458.1
[58] Field of Search ................................. 250/584, 585, 250/586, 458.1, 484.4; 356/417

[56] References Cited

U.S. PATENT DOCUMENTS

| | | |
|---|---|---|
| 4,786,813 | 11/1988 | Svanberg et al. . |
| 5,062,942 | 11/1991 | Kambara et al. . |
| 5,069,769 | 12/1991 | Fujimiya et al. . |
| 5,138,170 | 8/1992 | Noguchi et al. . |

(List continued on next page.)

FOREIGN PATENT DOCUMENTS

| | | |
|---|---|---|
| 2 024 412 | 1/1980 | United Kingdom . |
| WO 90/10219 | 9/1990 | WIPO . |
| WO 96/18205 | 6/1996 | WIPO . |

OTHER PUBLICATIONS

T. Reid, et al., "Simultaneous Visualization of Seven Different DNA Probes by in situ Hybridization Using Combinatorial Fluorescence and Digital Imaging Microscopy" *Proc. Natl. Acad. Sci., USA*, (Feb. 1992) vol. 89, pp. 1388–1392.

R.M. Cothren, et al., "Gastrointestinal Tissue Diagnostics by Laser–Induced Fluorescence Spectroscopy at Endoscopy," *Gastrointestinal Endoscopy*, vol. 36, No. 2, (Mar./Apr. 1990), pp. 105–111.

(List continued on next page.)

*Primary Examiner*—Edward P. Westin
*Assistant Examiner*—Richard Hanig
*Attorney, Agent, or Firm*—David G. Beck; Townsend and Townsend and Crew, LLP

[57] ABSTRACT

An apparatus capable of measuring quantities of biological or other types of samples that have been labeled using any of a variety of techniques including fluorescence, radioisotopes, enzyme activated light emitting chemicals, and enzyme activated fluorescent materials is provided. The apparatus allows for either simultaneous or sequential acquisition of signals from multiple sample types. The apparatus is not restricted to a particular source or wavelength of excitation or readout light, nor is the apparatus restricted to a particular emission wavelength. The provided scanner includes a source module that preferably contains an internal laser emitting two different wavelengths of approximately the same intensity. An optional external light source may be coupled to the source module, thus adding further flexibility through the addition of other wavelengths (e.g., V, visible, mid-IR, and IR). The scanner also includes a detection module. Within the detection module are two detectors, thus allowing the simultaneous detection of multiple wavelengths. A bifurcated optical cable is used to transfer the excitation and/or readout light from the source module to the sample and subsequently transfer the emitted and/or scattered light from the sample to the detection module. The scanning stage of the scanner is designed to accommodate a variety of samples, ranging from phosphor screens, gels, and fluorescent samples to microtiter plates. An internal microprocessor is used to control the various aspects of the scanner, preferably including translation stage control, source filters, and detection filters. The internal microprocessor may be coupled to an external computer. The external computer may be used to change the programming of the microprocessor, provide a user interface to the microprocessor, process and store test results, and display sample images.

45 Claims, 7 Drawing Sheets

U.S. PATENT DOCUMENTS

| | | |
|---|---|---|
| 5,190,632 | 3/1993 | Fujimiya et al. . |
| 5,213,673 | 5/1993 | Fujimiya et al. . |
| 5,246,866 | 9/1993 | Nasu et al. . |
| 5,266,803 | 11/1993 | Heffelfinger . |
| 5,290,419 | 3/1994 | Kambara et al. . |
| 5,424,841 | 6/1995 | Van Gelder et al. . |
| 5,436,718 | 7/1995 | Fernandes et al. . |
| 5,459,325 | 10/1995 | Hueton et al. . |
| 5,461,240 | 10/1995 | Karasawa ................................ 250/585 |
| 5,528,050 | 6/1996 | Miller et al. . |
| 5,578,818 | 11/1996 | Kain et al. . |
| 5,591,981 | 1/1997 | Heffelfinger et al. . |
| 5,780,857 | 7/1998 | Harju et al. . |

OTHER PUBLICATIONS

P.S. Anderson, et al., "Autofluorescence of Various Rodent Tissues and Human Skin Tumour Samples," *Lasers in Medical Science*, vol. 2, No. 1 (Jan.–Mar. 1987), pp. 41–49.

J..Z. Sanders, et al., "Imaging as a Tool for Improving Length and Accuracy of Sequence Analysis in Automated Fluorescence–Based DNA Sequencing," *Electrophoresis* No. 12, (1991), pp. 3–11.

Product Literature for STORM Gel and Blot Imaging System produced by Molecular Dynamics. ©1995 Molecular Dynamics, Inc.

Product Catalogue for Life Science Solutions produced by Molecular Dynamics. ©1995 Molecular Dynamics, Inc.

MULTI PARAMETER SCANNER

CROSS REFERENCE TO RELATED APPLICATIONS

This application is a Continuation-In-Part of U.S. Provisional application Ser. No. 60/055,567 filed Aug. 13, 1997, the complete disclosure of which is incorporated herein by reference for all purposes. This application is related to commonly assigned U.S. Pat. Nos. 5,591,981, issued Jan. 7, 1997 and 5,266,803, issued Nov. 30, 1993 and to commonly assigned, U.S. patent application Ser. Nos. 08/585,303, filed Jan. 11, 1996 now U.S. Pat. No. 5,863,504, 08/729,111, filed Oct. 11, 1996 now U.S. Pat. No. 5,784,152, and to 08/927,556, filed Sep. 9, 1997 now U.S. Pat. No. 5,885,531, the complete disclosures of which are incorporated herein by reference for all purposes.

FIELD OF THE INVENTION

The present invention relates generally to optical scanners and, more particularly, to a method and apparatus for measuring and/or imaging biological or other types of samples that have been labeled using a variety of techniques.

BACKGROUND OF THE INVENTION

Imaging is an important tool used in the detection of a variety of biological molecules. For example, imaging devices may be used to detect and determine concentrations of molecules of a specific molecular weight, DNA, a specific DNA sequence, proteins, and carbohydrates. Typically the samples of interest are labeled using fluorescent dyes, radioisotopes, or enzyme activated light emitting (i.e., chemiluminescent) or fluorescent (i.e., chemifluorescent) chemicals.

UV, visible or IR light excites fluorescent dyes and markers. Once excited the dyes fluoresce, preferably emitting light at a wavelength distinguishable from the excitation wavelength. Radioactive and chemiluminescent signals are typically captured using either x-ray film or storage phosphor screens. The x-ray film is developed and read using a densitometer. The storage phosphor screen does not require development and is read out by scanning the screen with a beam of light. The readout beam produces an emission from the storage phosphor, the intensity of the emission being proportional to the original quantity of radiation retained by the storage phosphors.

A variety of devices have been described for use in detecting labeled biological samples. U.S. Pat. No. 3,746,840 discloses a device for high-resolution readout of information stored on a film. The device comprises a slit equal in width to the desired resolution with optical fibers behind the slit of a diameter equal to the slit width. The optical fibers collect the light as it crosses the slit and transmits it to the detectors.

U.S. Pat. No. 3,836,225 discloses a fiber optic laser scanner. The disclosed scanner uses two optical fiber sets attached to electromagnetic coils. The magnetic coils deflect the beam as required.

U.S. Pat. No. 3,892,468 discloses a passive array of variable length optical fibers that function as a dynamic scanner. Each consecutive fiber in the fiber array is incrementally longer than the preceding fiber. Thus light entering the fibers at the same time will exit the fibers at different times, the variations in exit times thus being correlated with different locations.

U.S. Pat. No. 4,877,966, discloses a device for measurement of low-level laser induced phosphorescence. The laser is directed through a beam expander and then aimed by mirrors. The induced phosphorescence is collected by a fiber optic face plate and passed to a photomultiplier tube.

U.S. Pat. No. 5,062,942 discloses a fluorescence detection system for use with electrophoresis gel plates. In the disclosed system the gel plate is illuminated with a laser excitation source and the emitted fluorescent light is separated into a plurality of virtual images that are subsequently passed through individual bandpass filters thereby providing multicolor fluorescence detection.

U.S. Pat. No. 5,290,419 discloses a multicolor fluorescence detection system utilizing multiple laser sources and means for detecting fluorescence as a function of wavelength. The individual laser sources are combined with a light chopper (e.g., rotary shutter) in order to irradiate the sample on a time-sharing basis.

U.S. Pat. No. 5,436,718 discloses a multi-function photometer for measuring the absorbance, fluorescence, and luminescence associated with a sample. The disclosed system uses optical fibers to transmit light to and from the sample using scanning head. A computer controlled positioning table is used to position the canning head with respect to the samples contained in a microplate.

U.S. Pat. No. 5,459,325 discloses a high-speed fluorescence scanner. The system utilizes a lightweight scan head to scan a collimated excitation beam across the sample. The emitted fluorescence is gathered by the scan head lens and directed back along the optical path of the excitation beam to a detector. In order to obtain a two-dimensional image of the sample, the sample is translated in an axis orthogonal to the scan line.

In a publication entitled *Imaging as a Tool for Improving Length and Accuracy of Sequence Analysis in Automated Fluorescence-Based DNA Sequencing* by Sanders et al, a method of signal analysis is disclosed. (*Electrophoresis* 1991, 12, 3–11). In the disclosed method, a computer program was used to remove distortions in the DNA bands in sequencing gels, thus improving the accuracy of DNA sequence analysis. The authors noted that the disclosed techniques should be applicable to other systems such as gel electrophoresis of proteins and DNA restriction fragments.

The scanners described above do not take full advantage of the wide range of different sample types available. Rather, a typical scanning device is designed for a specific type of sample, e.g., fluorescent samples, and as a result is incapable of use with another type of sample. In addition, many biological sample scanners offer a very limited set of irradiation/excitation wavelengths and/or emission wavelengths, thus further limiting the functionality of the device. Lastly, the resolution offered by many, if not all, of the fore-mentioned markers is not fully utilized by most biological sample scanning systems.

Therefore a compact optical scanner capable of use with a variety of sample types and configurations that offers multiple excitation/irradiation wavelengths and that may be used to detect emissions at a variety of wavelengths is desirable.

SUMMARY OF THE INVENTION

The present invention provides an apparatus capable of measuring quantities of biological or other types of samples that have been labeled using any of a variety of techniques including fluorescence, radioisotopes, enzyme activated light emitting chemicals, and enzyme activated fluorescent materials. The apparatus allows for either simultaneous or sequential acquisition of signals from multiple sample types.

The apparatus is not restricted to a particular source or wavelength of excitation or readout light, nor is the apparatus restricted to a particular emission wavelength. Thus the present invention is capable of measuring every type of fluorescent dye, storage phosphor screen, and chemiluminscent probe.

In one aspect of the invention, the scanner includes a source module. The source module has an internal laser that emits two wavelengths, 532 nanometers and 1064 nanometers, of approximately the same intensity. These two wavelengths allow the scanner to function with storage phosphor screens based on BaFBr:Eu, SrS:Ce, and SrS:Sm as well as a variety of fluorescent dyes and other stains. An optional external light source may be easily coupled to the source module, thus adding further flexibility to the scanner's potential applications through the addition of other wavelengths in the UV, visible, mid-IR, and IR spectral ranges. The external light source passes through a beam splitter that combines the emissions from the internal laser with those of the external source(s). The light emitted by the external source undergoes an auto-alignment procedure to insure optimal coupling between the source and the optical system of the scanner.

In another aspect of the invention, the scanner includes a detection module. Within the detection module are two detectors, thus allowing the simultaneous detection of multiple wavelengths. A variety of bandpass filters and beam splitters contained in at least two filter wheels provide the means of removing undesired radiation from the light beam prior to detection. Preferably the two detectors are photomultiplier tubes, thus providing high sensitivity over a relatively wide wavelength range.

A bifurcated optical cable is preferably used to transfer the excitation and/or readout light from the source module to the sample and subsequently transfer the emitted and/or scattered light from the sample to the detection module. Although neither the number nor the physical arrangement of the fibers is critical, typically between 1 and 10 excitation fibers are surrounded by between 100 and 300 collection fibers in order to form the scanning head probe. Coupled to the end of the fiber scanning probe are focussing optics and condensing optics. In order to accommodate a range of sample sizes without adjusting the separation distance between the probe and the sample, preferably the probe optics provide a focal spot size of less than 150 micrometers over a 5 millimeter range. Alternatively, either the scanning head probe or the optics within the probe may be coupled to a translation stage, thus allowing the scanning probe to be optimized for different sample sizes.

In another aspect of the invention, the system includes a scanning stage for scanning the probe across the sample. The system is designed to accommodate a variety of samples and sample types, ranging from phosphor screens, gels, and fluorescent samples to microtiter plates. The scan head is mounted to a pair of translation stages, thus allowing the probe to scan the entire available sampling area or some subset thereof In one embodiment of the invention, the scanning system operates in a closed loop fashion, thereby providing direct position feedback. Positional information may be obtained using optical encoders, either mounted within the motors operating the translation stages or mounted in such a way as to monitor stage travel of the individual translation stages.

In another aspect of the invention, a microprocessor controls the scanning system. In one embodiment the microprocessor controls motors coupled to the scanner's translation stages, thus allowing the microprocessor to control the scan speed as well as the sampling area of the scanner. In another embodiment the microprocessor also controls the filter wheels in the source module and the filter wheels in the detector module. In yet another embodiment the microprocessor controls the high voltage supplies for photomultiplier tube detectors in the detection module, thus allowing the gain of the detectors to be varied depending upon the requirements imposed by the sample.

The microprocessor of the present invention may be coupled to an external computer. The external computer may be used to change the programming of the microprocessor, thus allowing the system to be altered as different detector modules, source modules, and external sources are added to the system. The external computer may also be used to provide the user with a means of programming the microprocessor for a specific test run, for example, for a specific sample type and size. In order to simplify programming, either the microprocessor or the external computer may include a look-up table containing a variety of operating parameters and/or programming instructions based on the intended conditions of operation (e.g., sample type, irradiation wavelengths, detection wavelengths, etc.). The external computer may also be used for test result storage as well as providing a means of processing and displaying the test results. The results may be displayed in a variety of formats, including tabular and sample image displays. The external computer may also be used to present the data in a manner that is more understandable by the user, for example, representing different emittance intensities or wavelengths by different colors.

A further understanding of the nature and advantages of the present invention may be realized by reference to the remaining portions of the specification and the drawings.

DETAILED DESCRIPTION OF THE INVENTION

Figure 1:
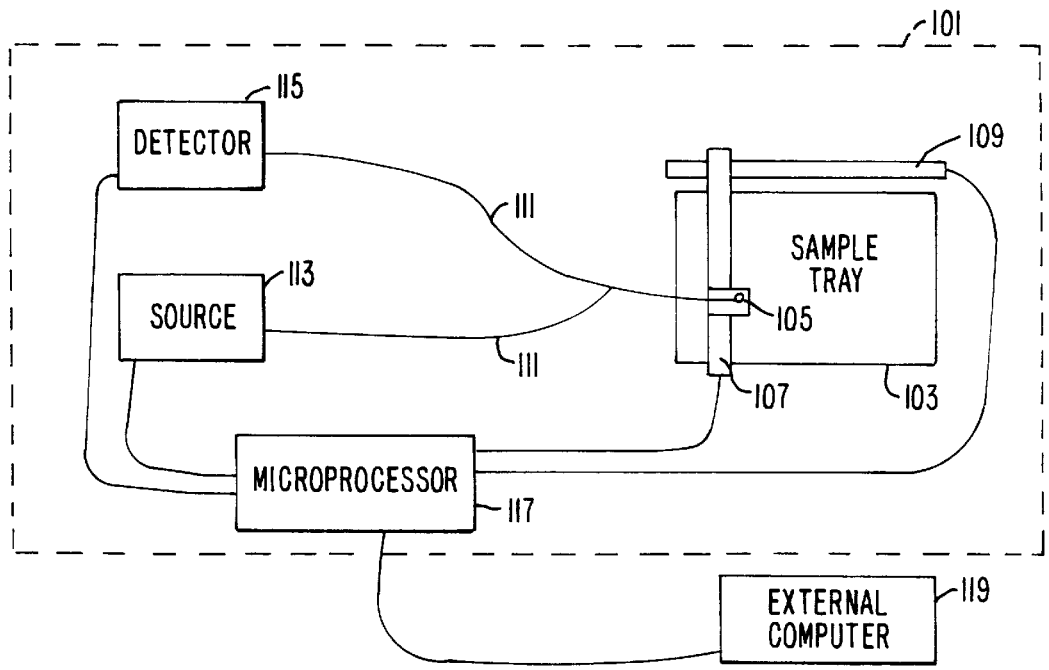
FIG. 1 schematically illustrates an overview of a scanner according to the present invention.

FIG. 1 schematically illustrates an overview of a scanner according to the present invention. Although a variety of external components may be attached to the system for added versatility, the principal system components are designed to fit within a compact, lightweight assembly 101. The sample of interest is placed on a sample tray 103 within assembly 101. Sample tray 103 is configured to hold a variety of sample types, thus adding to the versatility of the device. A scanner head 105 is movably coupled to a pair of translation members 107 and 109. Translation members 107 and 109 allow scanner head 105 to be scanned over the entire sample or any portion thereof.

An optical means 111 is coupled to scanner head 105, thereby allowing radiation from a source 113 to pass through scanner head 105 and impinge on a small, selected area of the sample held in sample holder 103 Preferably optical means 111 is comprised of a fiber optic, thus providing a simple means of coupling energy from source 113 to scanning head 105. Light emitted and/or scattered by the sample is collected at head 105, passed through optical means 111, and detected by a detection system 115. Alternatively, light passing through the sample and reflected from a reflective surface placed below the sample may be collected at head 105, passed through optical means 111, and detected by detection system 115, thus yielding a quantity that may be correlated to the absorption of the sample. Alternatively, the light reflected by the sample may be collected at head 105, passed through optical means 111, and detected by detection system 115. The means for coupling head 105 to source 113 may be different from the means for coupling head 105 to detection system 115, however preferably a bifurcated fiber optic is used such as that disclosed in U.S. Pat. No. 5,266,803, the disclosure of which is incorporated herein in its entirety.

A microprocessor 117, coupled to translation stages 107 and 109, is used to control the scanning operation, for example the scan speed. Microprocessor 117 is also coupled to source 113 and detection system 115. Although microprocessor 117 may be configured to independently operate the scanning system, it may also be coupled to an external computer system 119. External computer 119 may be used to program processor 117, monitor experimental progress, store test results, and construct and display sample images from the signals detected by system 115. External computer 119 may also be used in conjunction with processor 117 to control and manipulate the scanning process and the resultant data (e.g, automatic lane finding, automatic band finding, automatic quantitation of results, user-defined templates for automatic quantitation parameters, color correction, tiling memory management, etc.).

Figure 2:
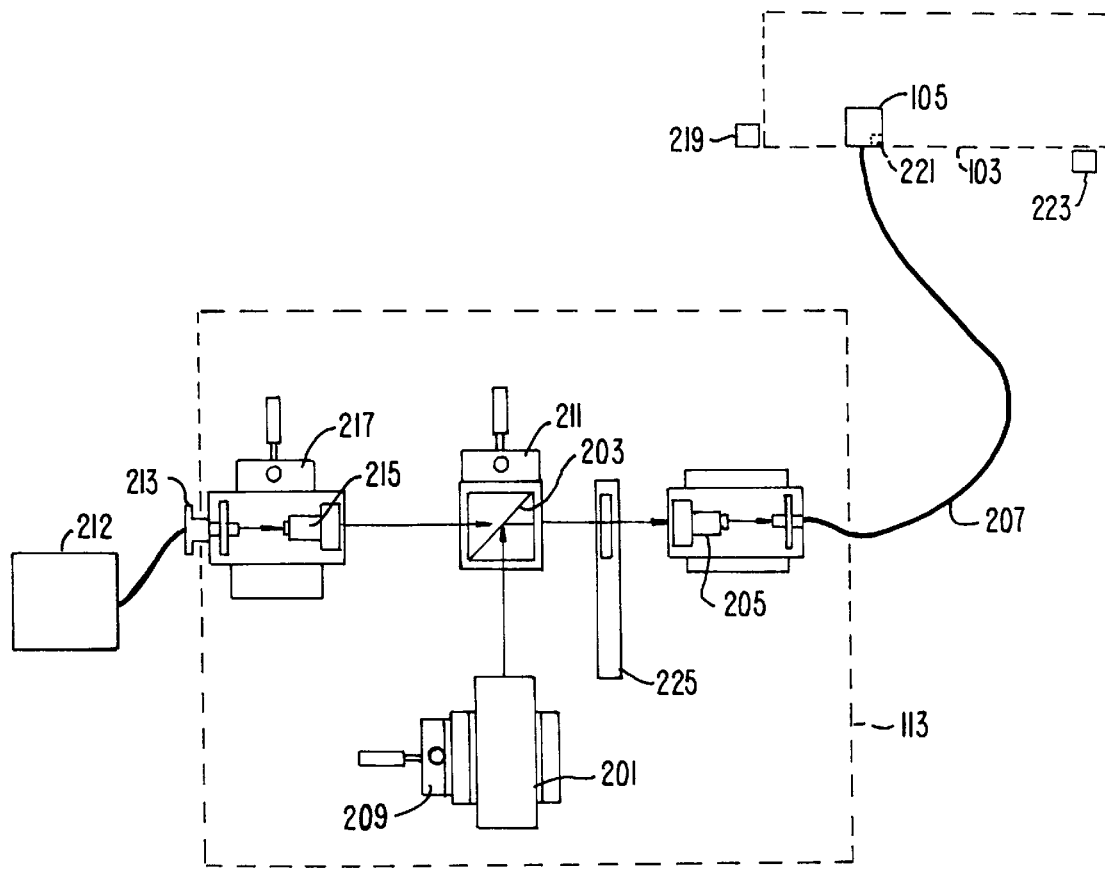
FIG. 2 is an illustration of the preferred embodiment of the source.

Although source 113 may be any of a variety of source types (e.g., laser, continuously tunable broadband source, etc.), the preferred embodiment of source 113 is illustrated in FIG. 2. Within source 113 is a dedicated laser 201 producing multiple wavelengths. The output intensity of laser 201 may be controlled by neutral density filters or by digitally controlling the power supply for the laser. Preferably laser 201 is a diode pumped solid state laser emitting light at 532 nanometers and at 1064 nanometers. The dual wavelength capabilities of laser 201 allow a wide range of samples to be excited without requiring any changes to the system. In the preferred embodiment, either the cavity mirrors of laser 201 or the coatings of the laser optics are designed such that the laser emits approximately the same energy intensity within the two selected wavelengths. By providing approximately the same output power, multiple types of phosphor screens can be efficiently scanned without requiring adjustments to the system. For example, storage phosphor screens based on BaFBr:Eu, SrS:Ce, and SrS:Sm may all be used with this source.

The light emitted by laser 201 is reflected by a beam combining mirror 203 into focussing assembly 205. Mirror 203 is designed to efficiently reflect both of the wavelengths emitted by laser 201. Assembly 205 focuses the reflected beam onto the end of fiber 207. Micro-positioners 209 and 211, coupled to laser 201 and mirror 203 respectively, are used to accurately locate the laser beam onto fiber 207, thus achieving the optimal transfer of energy from laser 201 through fiber 207 to the sample. Once laser 201 and mirror 203 have been properly located and locked into position, repositioning of these components is only required if one of them is inadvertently moved or if the laser beam exiting laser 201 exhibits movement as the laser ages. However the preferred embodiment of the system is designed to minimize if not altogether eliminate the need for positional adjustment by the user.

In order to provide additional flexibility as well as the potential for use with as-yet undiscovered samples and targets, the preferred embodiment of source 113 provides for an external source 212. External source 212 is coupled to the scanning system through an external port 213. The light from the external source passes through port 213 to a collimating assembly 215. Collimating assembly 215 collimates the light from external source 212 and passes the collimated light through beam combining mirror 203 and focussing assembly 205 into fiber 207. The optical coatings on mirror 203 are designed to maximize reflection at the desired wavelengths emitted by laser 201 while simultaneously maximizing transmittance of all other wavelengths, particularly the wavelengths of potential interest for an external source. Thus multiple excitation wavelengths may be simultaneously transmitted through fiber 207 to the sample, i.e., dual wavelengths from laser source 201 and one or more wavelengths from one or more external source(s) 212.

A variety of external sources 212 may be coupled to external port 213. Both lasers and broadband sources may be coupled into the scanning system, depending upon the desired wavelength(s). Generally, the external source may be any source of ultraviolet (i.e., UV), visible, near infrared (i.e., NIR), or infrared (i.e., IR) radiation. Thus the external source may be continuously tunable or not, pulsed or continuous, coherent or incoherent, and be in the form of a laser or an arc lamp or some other source emitting the desired radiation.

As discussed above, dual wavelength internal laser source 201 may be used with storage phosphor screens based on BaFBr:Eu, SrS:Ce, and SrS:Sm. In addition, internal source 201 may be used with a variety of dyes, stains, fluorescent, and chemiluminescent markers, depending upon the required excitation wavelength. Potential dyes for use with the 532 nanometer line, and therefore not requiring an external source, include the following fluorescent dyes; JOE, TAMRA, ROX, HEX, Bodipy, TRITC, CY3, Rhodamine B, and Lissamine Rhodamine. In addition, this wavelength laser line may be used to excite DNA stains based on Ethidium Bromide, Ethidium homodimer, POPO-3, Radiant Red as well as protein stain Sypro Red. Additionally a variety of external sources may be coupled to port 213 and used with a variety of dyes/stains. For example, the 488 nanometer line emitted by Argon and Argon/Krypton lasers may be coupled to external port 213 and potentially used with fluorescent dyes (e.g., FAM, Bodipy FL, Lucifer Yellow, NBD-X Nile Red, Oregon Green, CY2, TET, HEX R6G, JOE, and FITC), SS stains (e.g., SYBR Green II, Radiant Red, YOYO-1, and TOTO-1), protein dyes (e.g., Nile Red and SYPRO Orange), and DNA stains (e.g., Pico Green, Vistra Green, SYBR Green I, YOYO-1, and TOTO-1). Two other well known dyes, CY5 and CY7, require excitation in the 650 nanometer range and therefore a potentially suitable laser is an Argon/Krypton laser emitting at the 647 line. Other potential laser sources include HeNe lasers, operating either in the red or green, and frequency doubled YAG lasers. This list of potential external sources matched to various dyes and stains is intended for illustrative purposes only, and is not intended to be exhaustive. The design of the present invention is such that the number and type of different sources that may be coupled through port 213 into the scanner is practically limitless.

External port 213 typically does not provide sufficient precision to optimally couple external source 212 to the scanning system. Therefore preferably a translation stage system 217 is coupled to collimating assembly 215 thus allowing the emission from external source 212 to be optimally coupled to the scanner. Although stage 217 may be manually operated, preferably stage 217 is controlled by microprocessor 117, thereby allowing for auto-alignment of the optical system.

A variety of alignment algorithms may be used to optimize the optical throughput of the external source. The alignment may be performed on a periodic basis, prior to each scan, or only after the initial coupling of external source 212 to port 213. Basically translation stage 217 must be moved until the maximum amount of energy from external source 212 passes through collimating assembly 215 and into focussing assembly 205. In one embodiment of the invention, stage 217 initially undergoes a rough adjustment feedback loop simply to find the general preferred location of collimator 215. Following the rough adjustment, a fine adjustment feedback loop determines the optimum stage location. The auto-alignment procedure may be as simple as moving the stage in predefined incremental steps in a raster scanning fashion while recording the coupling efficiency at each step. After the raster scan is complete, the stage may be moved back to the location offering the highest efficiency and the raster scan can then be repeated using smaller incremental steps. Although this process may be repeated numerous times, in the preferred embodiment a single rough scan followed by a single fine scan has been determined to be adequate. In order to minimize the storage capacity used to store the coupling efficiency noted for each position of stage 217, the system may be programmed to discard coupling efficiencies below a predefined efficiency. Alternatively, the system may be designed to discard coupling efficiency samples that fall sufficiently below a previously monitored coupling efficiency.

Several different methods of monitoring the coupling efficiency of external source 212 to fiber 207 and ultimately, the sample, may be used. In one embodiment scanning head 105 is moved to a portion of the scanning module that contains a dedicated detector 219. As stage 217 is adjusted, the energy falling on detector 219 is monitored thereby providing feedback on the coupling of the external source to the optical system. In another embodiment, a calibration detector 221 may be located directly on scan head 105. A flip mirror or a stationary mirror may be used to couple some portion of the output of fiber 207 to detector 221. In the preferred embodiment, detection system 115 is used. In this embodiment preferably scan head 105 is first moved to a calibration site 223 on the scanning table, thus insuring that sufficient energy passes through the entire assembly to detector 115 to allow optimization of stage 217. Calibration site 223 may be a simple broad band reflector, thus reflecting the energy from external source 212 back through fiber 111 to detector 115.

Source 113 also contains a filter wheel 225. Filter wheel 225 contains numerous filters, the selection of which is provided by rotating the wheel. Preferably filter wheel 225 is coupled to microprocessor 117, thus allowing further automation of the system. The filters within wheel 225 typically are used to limit the radiation passing through fiber 207 to the sample and possibly being scattered to the detection system. For example, although laser 201 preferably emits radiation at the desired dual wavelengths of 532 and 1064 nanometers, it may also emit minor amounts of radiation at various other wavelengths, e.g., laser harmonics. These harmonics may impact the performance of the scanner, for example by being mistaken by detection system 115 as emissions from the sample thereby providing an erroneous signal. A filter within filter wheel 225 may be used to block such laser harmonics. Besides containing filters, filter wheel 225 may also contain neutral density filters to control the intensity of the source as well as an opaque member for use as an optical shutter. The opaque member would allow the system to control whether radiation from either laser 201 or external source 212 is allowed to pass through fiber 207 to the sample.

Figure 3:
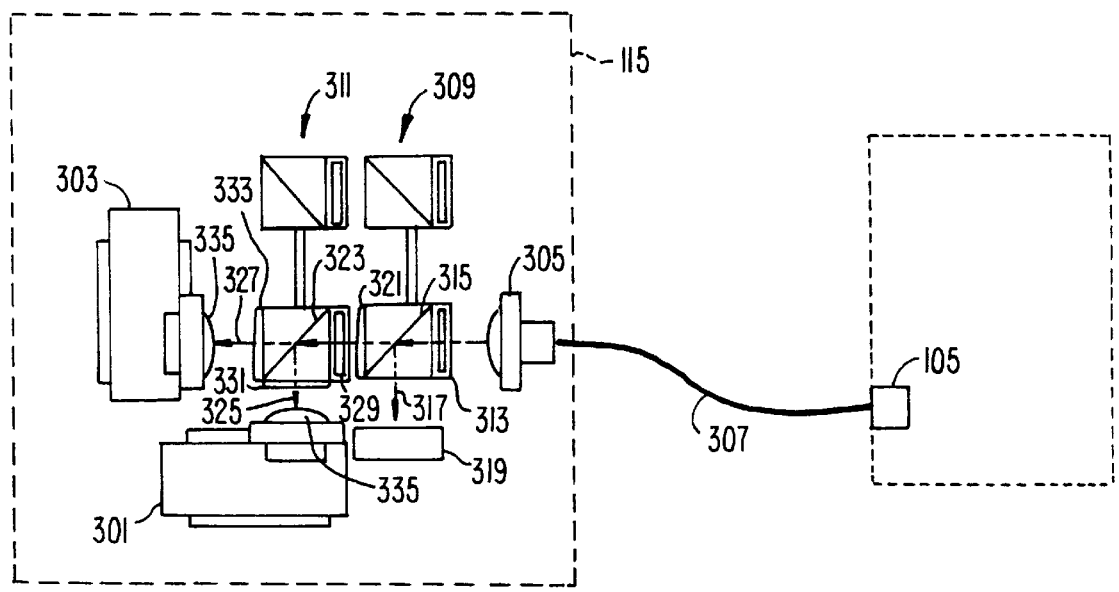
FIG. 3 is an illustration of the preferred embodiment of the detection system.

FIG. 3 is an illustration of the preferred embodiment of detection system 115. Preferably detection system 115 is provided as a module within the system housing, thus allowing it to be easily and quickly replaced if the present system breaks or if a different detection system provides additional benefits (e.g., higher sensitivity in the wavelength regions of interest, continuous tunability, etc.). Within detection system 115 are two individual detectors, 301 and 303. The inclusion of two detectors allows the system to simultaneously detect two different wavelengths, thus providing twice the available information per scan. For example, the two different detection wavelengths may be used to detect two different emission wavelengths, e.g. the emissions due to two different dyes or stains. The two different dyes or stains may be excited by a single wavelength, or by multiple wavelengths emitted by laser source 201, external source 212, or by some combination thereof.

The light picked up by scanning head 105 is transmitted to a collimating lens assembly 305, preferably using a fiber bundle 307. The light passing through assembly 305 passes through two filter wheels, 309 and 311, prior to being detected. In the preferred embodiment, each filter slot of each filter wheel contains both dichroic beam splitters and dichroic bandpass filters. For example, in the embodiment illustrated in FIG. 3, the light from assembly 305 first passes through a bandpass filter 313. Filter 313 is used to remove unwanted radiation from the light beam prior to it being detected. The light beam then passes through beam splitter 315. Preferably beam splitter 315 reflects the excitation wavelength along a path 317, preferably allowing the reflected light to then pass into a beam dump 319. Reflecting the excitation wavelength out of the beam path minimizes the possibility of this light passing back through the system and impacting the overall system performance. Filter 313 may be placed before beam splitter 315 as shown, or after beam splitter 315. If necessary an additional bandpass filter 321 may be used in conjunction with filter 313 and splitter 315.

After the initial conditioning of the beam through the filters contained in filter wheel 309, the light passes through a second filter wheel 311. In the preferred embodiment, each filter slot of wheel 311 contains a dichroic beam splitter 323. Splitter 323 splits the incoming beam into two beams 325 and 327. Beam 325 is reflected into detector 301 while beam 327 is passed through to detector 303. If necessary, a filter 329 may be placed in front of splitter 323 and used to remove undesirable radiation from being detected by either detector. For example, filter 329 may be used to remove excitation light that was not completely reflected by beam splitter 315. In addition, filters may be placed at locations 331 and 333 in order to remove further undesirable radiation from being detected by detectors 301 and 303, respectively.

Preferably both filter wheels 309 and 311 are coupled to processor 117, thus allowing the system to be more fully automated. However, the filter wheels may be manually controlled as well, thus allowing the user to manually place the desired filters in the proper locations.

In the embodiment of the detection system illustrated in FIG. 3, coupled to each detector is a focussing lens assembly 335. Lens assemblies 335 focus the radiation onto the respective detectors. A variety of different detectors may be used, primarily depending upon the intended use of the scanning system. Preferably detectors 301 and 303 are photomultiplier tube detectors, thus providing high sensitivity over a relatively wide wavelength range. By coupling the high voltage supplies of detectors 301 and 303 to processor 117, the gain of the detectors may be individually optimized, either prior to or during a scan. Furthermore processor 117, typically in conjunction with computer 119, may be used to construct composite images wherein the individual images are based on different detector gain settings.

Figure 4:
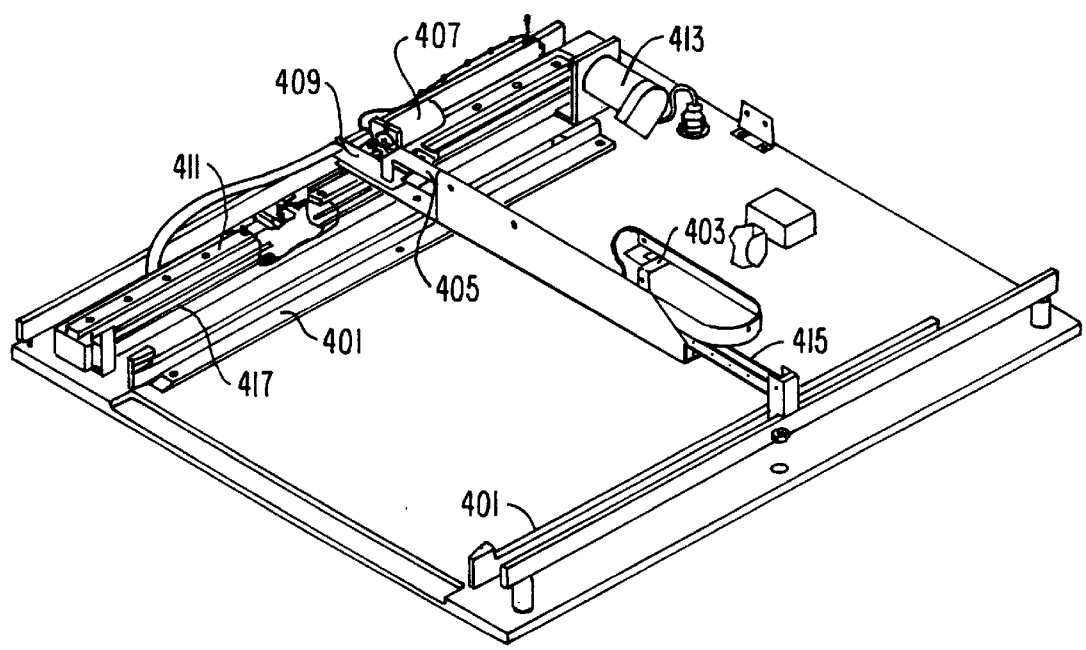
FIG. 4 is an illustration of the scanning mechanism of the preferred embodiment.

FIG. 4 is an illustration of the scanning mechanism of the preferred embodiment. In this embodiment the sample to be scanned is slid between and over a pair of sample positioning rails 401. Scan head 105, not shown in this illustration, is coupled to a scan head mount 403. Mount 403 moves along translation arm 405 under the power of scanning motor 407. The entire translation arm assembly 409 moves along a second translation arm 411. A second scanning motor 413 controls movement of arm assembly 409 along arm 411. In this embodiment scanning motors 407 and 413 are coupled to mount 403 and arm assembly 409, respectively, by belts 415 and 417. Both scanning motors are coupled to and controlled by microprocessor 117.

Translation arms 405 and 411 may be used to scan the sample area in a variety of patterns. For example, the translation arms may be used to move scan head 105 in a "Z" pattern across the entire sample area. In other words, scan head 105 may be moved in a first direction across the sample, then moved a small distance in a direction perpendicular to the first direction, and then moved back across the sample in a second direction opposite the first direction, this process being repeating until the entire sample is scanned. Alternatively, the scanning process along arm 405 may always occur in the same direction, i.e., from left to right. Either the entire sample or one or more subsections of the sample area may be scanned.

In one embodiment of the scanning mechanism, motors 407 and 413 are stepping motors and the system is run in an open loop fashion. In this embodiment the motors move scan head 105 to a first position and a sample is taken. Then the motors move scan head 105 in a step-wise fashion to a next position and another sample is taken. This process continues until the desired scanning pattern has been completed.

The preferred embodiment of the system operates in a closed loop fashion, thereby providing position feedback information to the system. In order to accomplish this operation, a film strip is attached to arm 405 that includes a series of accurately positioned lines. In this embodiment the frequency of lines is set at 5 lines per millimeter. An optical encoder mounted to mount 403 monitors the line markings on the film strip, thus providing the absolute position of scan head 105. Preferably whenever the optical encoder detects a line marking it splits the signal into a quadrature signal that is then used to trigger the electronics. Therefore as opposed to scanning at 5 lines per millimeter, the system scans at 20 lines per millimeter along the fast axis of the scan. A rotory encoder within motor 413 provides positional information for the slow axis of the scan, i.e., for arm assembly 409 moving along arm 411. Preferably the user may select the scan speed along both axes, and thus the system resolution, typically by inputting the desired resolution into microprocessor 117.

Figure 5:
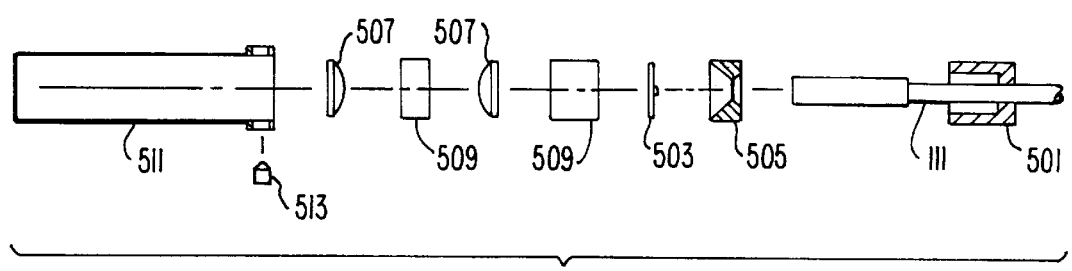
FIG. 5 is an expanded view of the preferred embodiment of the scan head.

FIG. 5 is an expanded view of the preferred embodiment of scan head 105. Bifurcated composite fiber 111 includes both fiber 207 for transmitting excitation radiation from source 113 to the sample and fiber bundle 307 for receiving sample emissions. Fiber assembly 111 is mounted within an optical fiber retainer 501. A focussing lens 503 is mounted adjacent to fiber 111, separated by a spacer 505. A pair of condensing lenses 507 is mounted within head 105 using a pair of spacers 509. The entire optical assembly is mounted within an enclosure 511 and held in place with set screws 513.

In the preferred embodiment, fixed optics 503 and 507 within scan head 105 provide a sufficiently long depth of field to be useful for a wide range of applications. Preferably the system provides a focal spot size of less than 100 micrometers and less than 150 micrometers over a 5 millimeter range. Sample emissions are collected over as large a viewing cone as possible, preferably greater than 0.4 numerical aperture (i.e., NA).

In an alternate embodiment of the invention, scan head 105 is coupled to mount 403 using a translation stage. This translation stage allows head 105 to move in an orthogonal direction to translation stages 405 and 411, i.e., the z-axis. Movement along this axis allows even greater flexibility in the types and sizes of samples that the system can scan. Since this stage reduces the necessity for a large depth of field, the optics in this embodiment may be optimized to achieve a very small focal spot size with a very efficient viewing cone. The z-axis stage may either be used to alter the spacing of scan head 105 with relation to the sample or to alter the relative positions of the optics internal to the scan head, thus altering the focal length of the system.

Preferably if a z-axis translation stage is incorporated into the scanner, it is coupled to a motor controlled by microprocessor 117. By adding a simple system to determine the distance between the sample surface and the detector head, the process of adjusting the z-axis stage to optimize the system may be fully automated. Alternatively, a reference point on the sample holding tray may be used to determine the separation distance. Alternatively, a sample height detector that determines either the maximum sample height or the average sample height as the sample tray is inserted into the scanning system may be used to set the optimum scan head height. A variety of separation sensors well known by those of skill in the art may be used in order to automate the adjustment of the scan head height (e.g., acoustic or optical based separation detecting systems).

As stated above, preferably the invention utilizes bifurcated optical cable 111. At scan head 105, excitation fibers 207 are coupled into a single cable along with detecting fibers 307. Excitation fibers 207 and detection fibers 307 are separated at the distal end in order to couple to source 113 and detection system 115, respectively. The number of fibers in each group is not critical and may vary, as long as each group contains at least one such fiber. In general, the number of fibers in each group will not exceed about 300. In preferred embodiments of the invention, the number of excitation fibers 207 will range from about 1 to about 10 and the number of detection fibers 307 will range from about 50 to about 300. In particularly preferred embodiments, the number of fibers 207 will be less than the number of collecting fibers, and in the most preferred embodiments, only one excitation fiber 207 is included in the bundle while about 100 to about 200 detection fibers 307 are included.

Figure 6:
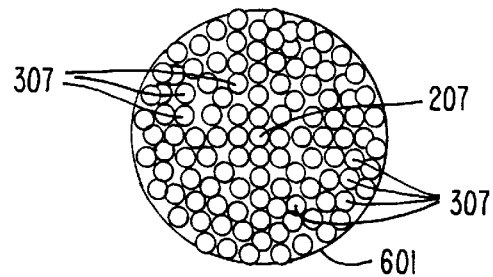
FIG. 6 illustrates the cross-section of the preferred embodiment of the optical fiber bundle.

The physical arrangement of the fibers in the bundle and the shape of the bundle cross-section are not critical. For example, excitation fibers 207 can be placed alongside detection fibers 307. In the preferred embodiment excitation fiber(s) 207 occupies the center of the bundle and is surrounded by detection fibers 307. This configuration typically offers the optimal collection efficiency. Generally circular bundle cross-sections are preferred. FIG. 6 illustrates a typical configuration in which excitation fiber 207 is surrounded by collection fibers 307, the entire bundle being surrounded by a protective sheath 601.

A cladding such as fused silica, glass, polyimide, other polymers, or the like individually surrounds excitation fiber(s) 207. Excitation fiber(s) 207 may have an internal diameter of 1 micrometer to 1,000 micrometers, preferably 50 micrometers. The intrinsic NA of fiber(s) 207 may be 0.1 to 0.5, usually 0.2 to 0.4, and preferably 0.2. However, this invention makes use of the technique described below to modify the intrinsic NA of excitation fiber(s) 207 to a lower value for optimal depth of focus and spot size.

The output NA of a fiber may be lowered in practice if the input NA is restricted to a lower value than the intrinsic NA of the fiber, and if the length of the fiber is such that additional spatial modes other than those coupled at the input are not allowed to propagate in the fiber. Thusly, even multimode fibers may be restricted in the actual modes that are allowed to propagate in the fiber. Accordingly, the output NA of excitation fiber(s) 207 may be restricted to values from 0.01 to 0.2, and preferably to 0.08.

A cladding such as fused silica, glass, polyimide, other polymers, or the like individually surrounds detection fiber(s) 307. Detection fiber(s) 307 may have an internal diameter of 10 micrometers to 1,000 micrometers, usually 10 micrometers to 200 micrometers, and preferably 200 micrometers. The NA of fiber(s) 307 may be 0.1 to 0.5, usually 0.2 to 0.4, and preferably 0.4.

As disclosed above, the present invention is designed for use with a variety of samples, ranging from phosphor plates to microtiter plates. Furthermore, the present invention may be used with samples of varying size. In the preferred embodiment of the invention, the bottom surface of the sample and/or sample tray is a rectangular plate that slides into the imager under user control along guides 401. Furthermore, in the preferred embodiment multiple samples may be placed on a single sample tray and inserted into the scanner along guides 401. For example, in one embodiment of the invention 8 microtiter plates may be placed on a single sample tray, each microtiter plate containing 1,536 individual sample wells, thus allowing 12,288 sample wells to be measured in a single scan. The sample holder may also be used with either thick or thin fluorescent samples, for example agarose gels, polyacrylamide gels, membranes, TLC plates, and sequencing plates.

Figure 7:
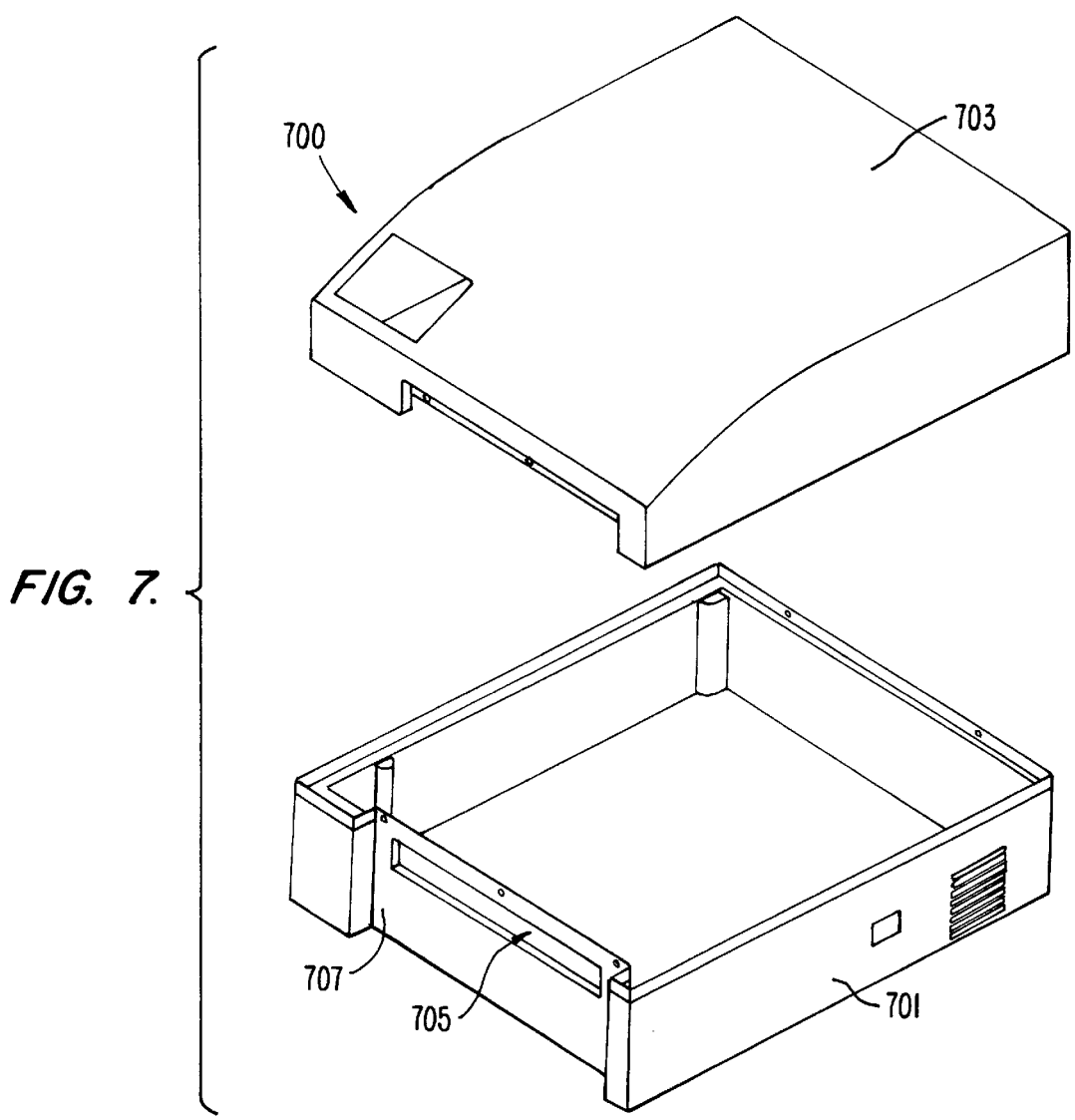
FIG. 7 illustrates the upper and lower enclosures for the preferred embodiment of the invention.

FIG. 7 is an illustration of a portion of a scanner enclosure 700 according to the preferred embodiment. Enclosure 700 includes a lower housing 701 and an upper housing 703. The translation arms 405 and 411 as well as the sample guides 401 are situated within housing 701 such that a sample plate to be placed within the scanner is slid through opening 705 and along guides 401. Since many samples are sensitive to outside light sources and further in view of the detection system potentially being influenced by outside light sources, enclosure 700 is preferably light tight.

Figure 8:
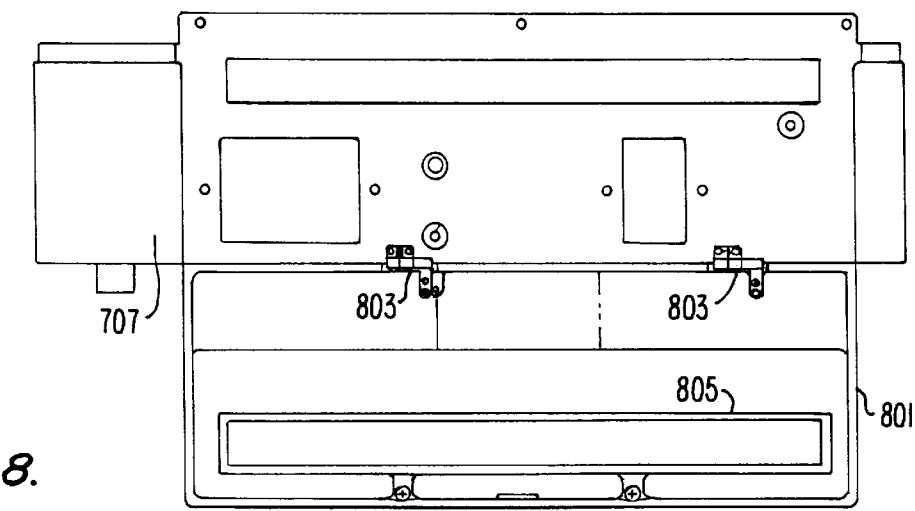
FIG. 8 illustrates an end view of the lower housing enclosure shown in FIG. 7.

To insure the elimination of outside light from entering enclosure 700, a door is preferably attached to side 707 of housing portion 701. FIG. 8 illustrates an end view of housing portion 701. A door 801 is coupled to end portion 707 with a pair of hinges 803. With door 801 closed, a light sealing gasket 805 surrounds opening 705, thus insuring that light cannot enter opening 705 during the scanning operation.

Figure 9:
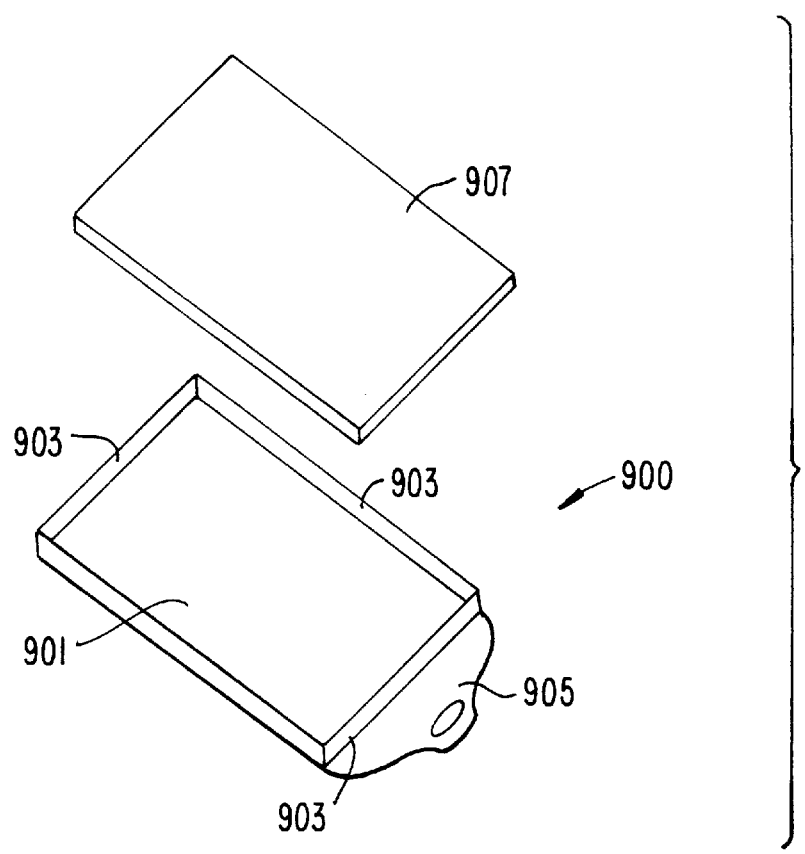
FIG. 9 illustrates one embodiment of a sample holding tray.

FIG. 9 illustrates one embodiment of a sample holding tray 900. One or more microtiter plates, sample chips (i.e., chips that contain a plurality of individual test samples at a plurality of locations per chip), gels, and other user-defined samples (e.g., DNA hybridization arrays, PCR arrays, etc.) are placed on a platform 901 of tray 900 prior to scanning. Platform 901 is sized to slide between guide rails 401. If necessary, platform 901 may include an extended border 903, thus helping the user to align the samples as well as minimize the risks of sample spillage into the scanner. A handle 905 allows the user to easily slide tray 900 into the scanner and remove it after testing has been completed.

Figure 10:
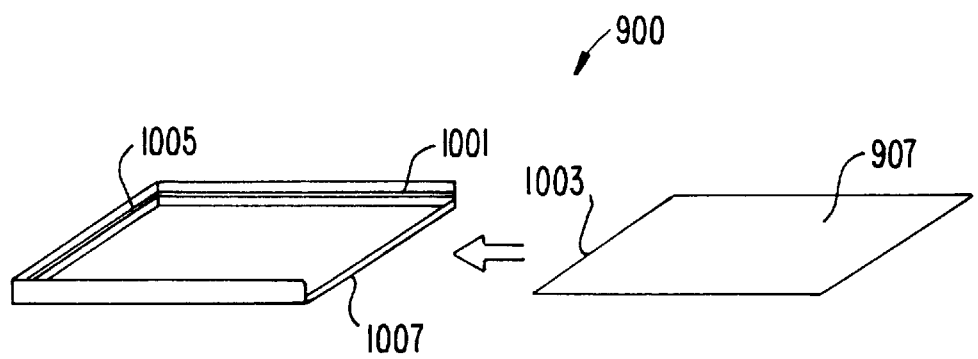
FIG. 10 illustrates an embodiment of a sample holding tray that includes a light cover.

In an alternate configuration of holding tray 900, a cover 907 is temporarily placed on top of platform 901, thus shielding samples placed on top of platform 901 from exterior light sources during transportation of tray 900 to and from the scanner. FIG. 10 illustrates one embodiment of this alternative configuration. In this embodiment top plate cover 907 slides into a pair of channels 1001 on either side tray 900. Once top plate cover 907 is in place, the leading edge 1003 of the cover fits into a channel 1005 at the rear portion of tray 900. Preferably a sealing gasket 1007 prevents light from reaching samples placed on platform 901 through the front of the tray. Sealing gasket 1007 may be spring loaded to insure a relatively light tight seal against top plate cover 907. In use, after tray 900 has been loaded into the scanner, cover 907 is withdrawn through opening 705, thus preparing the samples for scanning.

Figure 11:
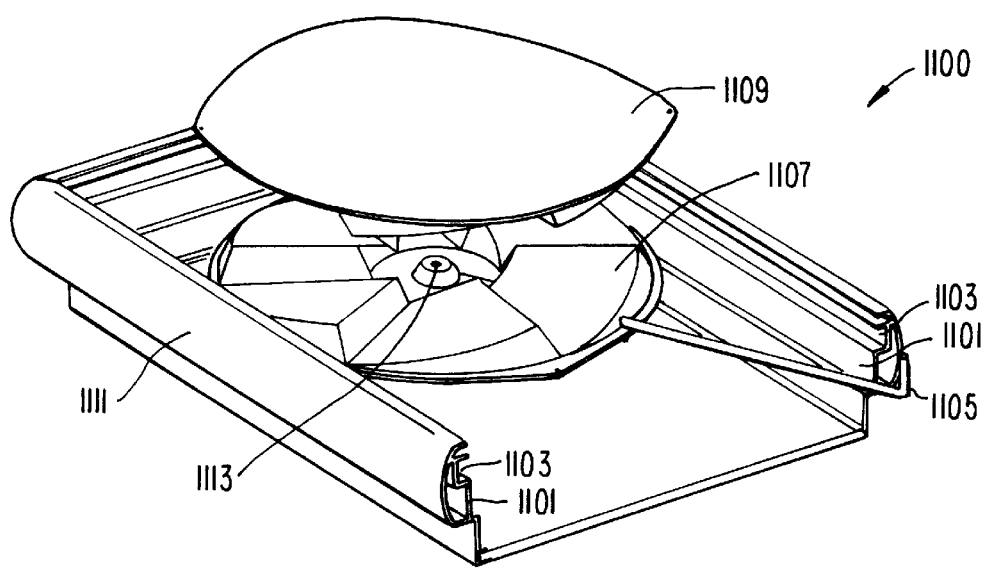
FIG. 11 illustrates a cross-section of a portion of a storage phosphor exposure platform.

FIG. 11 illustrates a cross-sectional view of a portion of a storage phosphor exposure platform 1100. The system is designed to allow the user to efficiently expose storage phosphor plates to a sample (e.g., a radioactively marked sample gel). If the storage phosphor plate is light sensitive, a sample tray similar to that shown in FIG. 10 may be used to keep the phosphor plate in an enclosed environment prior to and after exposure. By placing an appropriate seal or door at the front of exposure system 1100, light can be prevented from entering the system during exposure.

In use, a sample is inserted along channels 1101. The phosphor plate to be exposed is then inserted into channels 1103. If a light sensitive phosphor plate is being used, once the phosphor plate has been inserted into the light tight exposure platform, the light protective cover may be removed. Next the user moves control lever 1105, rotating wedge plate 1107 in a clockwise motion and raising the sample plate in channels 1101 to a position in which it is immediately adjacent to the surface of the phosphor storage plate in channels 1103. Once the sample plate has been moved to this position, a contact exposure may be made. At this point the user begins to time the exposure. After the exposure time has lapsed, lever 1105 is rotated counterclockwise and the storage phosphor plate is removed (after first replacing the light shield if a light sensitive plate is being used).

Figure 12:
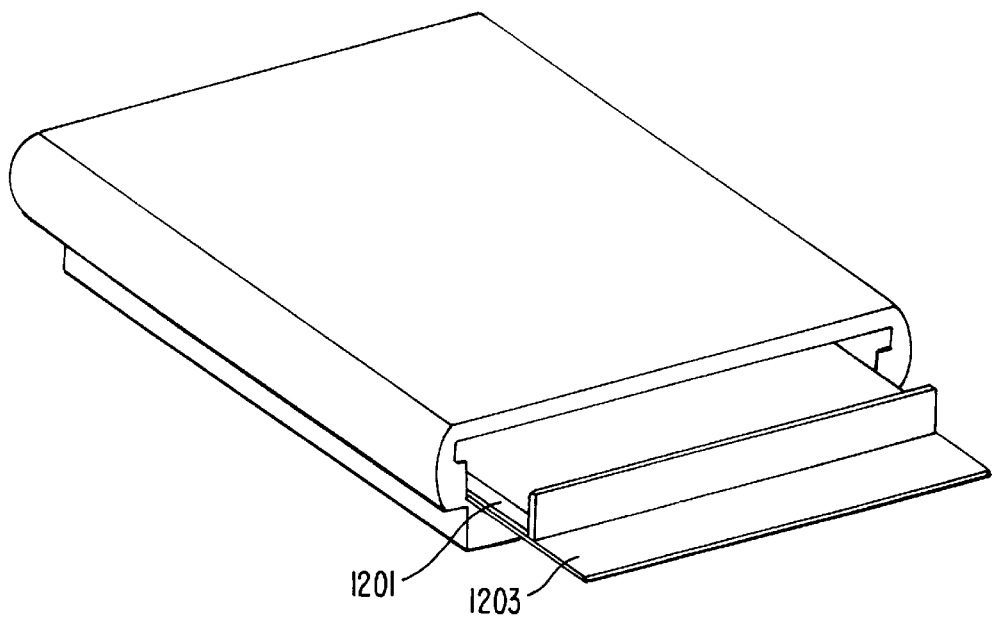
FIG. 12 illustrates an outer view of the storage phosphor exposure system shown in FIG. 11.
Figure 13:
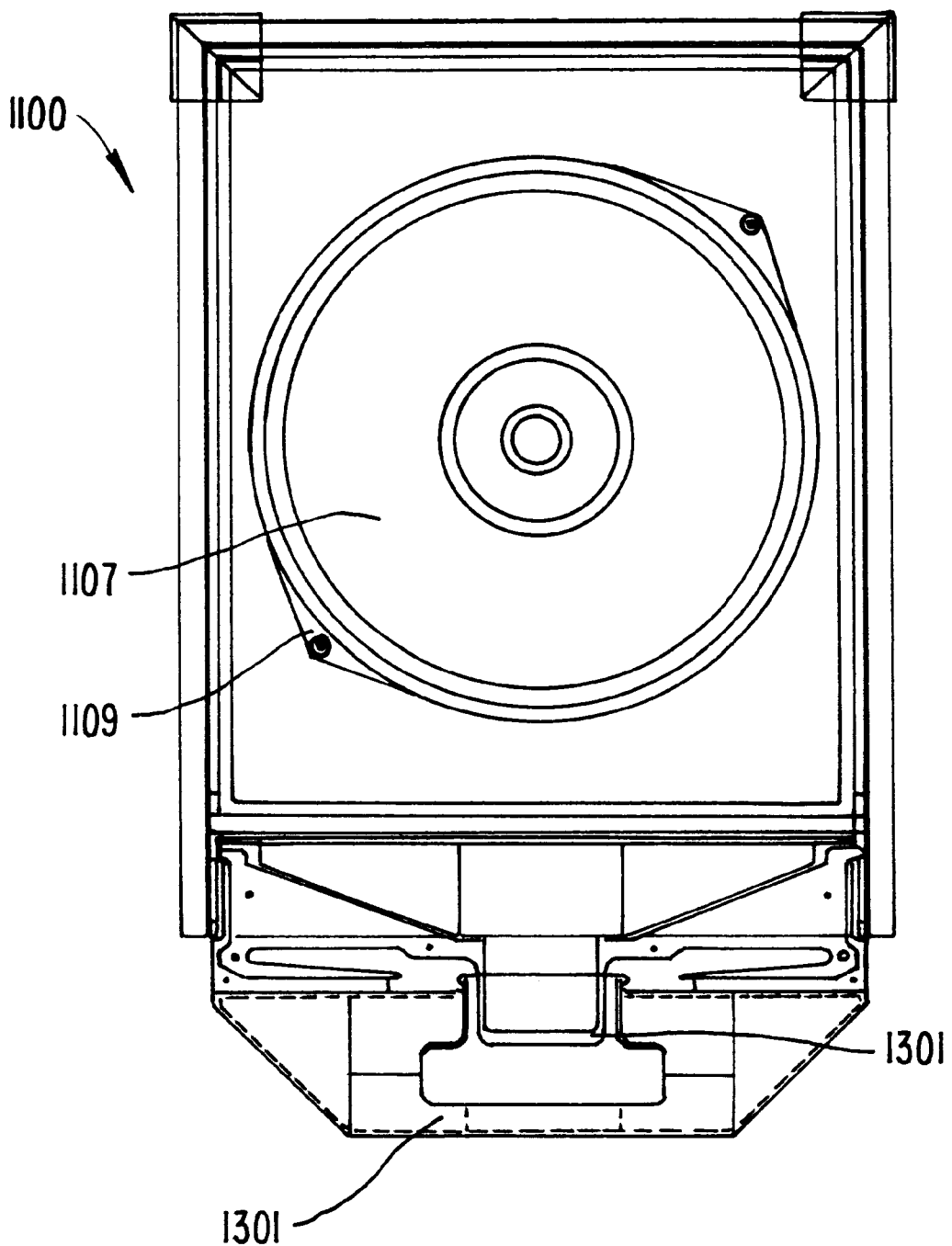
FIG. 13 illustrates an upper cross-sectional view of the storage phosphor exposure system shown in FIG. 11.

The movement of lever 1105 adjusts the position of a sample plate due to wedge plate 1107 and adjacent wedge plate 1109. Wedge plate 1107 is attached to the system enclosure 1111 at an axis point 1113. Adjacent plate 1109 is attached to a plate (not shown) that rests under the sample inserted along channels 1101. As plate 1111 is rotated clockwise, the wedges on plate 1107 and the adjacent wedges on plate 1109 push the upper surface of plate 1109 upward. By using several wedges on both plates 1107 and 1109, as lever 1105 is rotated in a clockwise direction the sample is moved upward in a uniform fashion. FIG. 12 illustrates an outer view of exposure system 1100. In the embodiment shown, a sample gel 1201 sitting on a sample plate 1203 is being inserted into exposure system 1100. FIG. 13 illustrates an upper cross-sectional view of system 1100. A handle assembly 1301 attached to a light sensitive phosphor plate allows the light protective cover to be easily removed from the light sensitive phosphor plate after it has been inserted into exposure system 1100. In this embodiment handle assembly 1301 is comprised of a pair of handles, one handle being attached to the cover plate and one handle being attached to the phosphor screen.

As will be understood by those familiar with the art, the present invention may be embodied in other specific forms without departing from the spirit or essential characteristics thereof Accordingly, disclosure of the preferred embodiment of the invention is intended to be illustrative, but not limiting, of the scope of the invention as set forth in the following claims.

What is claimed is:

1. A scanner system, comprising:
   a sample illumination source, wherein said illumination source is comprised of a laser, wherein said laser simultaneously emits radiation of a first wavelength and a second wavelength;
   a scan head for scanning an area of a sample held within a sample support, wherein said scanning is along a first direction and a second direction, wherein said scan head directs said radiation from said source to a portion of said sample;
   a detection system for monitoring radiation emitted by said sample, wherein said detection system comprises a first detector monitoring radiation of a third wavelength and a second detector monitoring radiation of a fourth wavelength, wherein said first and second detectors simultaneously monitor radiation emitted by said sample, and wherein each detector outputs a signal corresponding to the intensity of said radiation; and
   a wavelength selection system coupled to said detection system, wherein said wavelength selection system determines said third and fourth wavelengths of radiation monitored by said first and second detectors.

2. The scanner system of claim 1, further comprising:
   a first translation stage for moving said scan head in said first direction;
   a second translation stage for moving said scan head in said second direction; and
   a processor coupled to said first and second translation stages, said processor controlling movement of said scan head.

3. The scanner system of claim 2, further comprising a third translation stage coupled to said scan head, said third translation stage controlling motion of said scan head in a third direction, wherein said third direction is perpendicular to a plane formed by said first and second directions, and wherein said processor controls movement of said third translation stage.

4. The scanner system of claim 1, wherein said first and second detectors are photomultiplier tube detectors.

5. The scanner system of claim 4, further comprising a processor coupled to said first and second detectors, wherein said processor controls a first gain associated with said first detector and a second gain associated with said second detector.

6. The scanner system of claim 1, wherein a first intensity of said laser radiation of said first wavelength is approximately equal to a second intensity of said laser radiation of said second wavelength.

7. The scanner system of claim 1, wherein said wavelength selection system is further comprised of at least a beam splitter and a bandpass filter.

8. The scanner system of claim 1, wherein said wavelength selection system is further comprised of at least two beam splitters and at least two bandpass filters.

9. The scanner system of claim 1, further comprising a bifurcated bundle of optical fibers having distal and proximal ends, said optical fibers comprising at least one emitter fiber and at least one collecting fiber, said distal ends of said at least one emitter fiber and said at least one collecting fiber coupled to said scan head, wherein said radiation from said illumination source is focussed by a first focussing optic into said proximal end of said at least one emitter fiber, said radiation passing through said at least one emitter fiber and being focussed by a second focussing optic onto said portion of said sample, and wherein said radiation emitted by said portion of said sample is collected by a collection optic and focussed onto said distal end of said at least one collecting fiber, and wherein said proximal end of said at least one collecting fiber is positioned to pass said collected radiation to said detection system through said wavelength selection system.

10. The scanner system of claim 1, further comprising a filter wheel comprised of at least a plurality of optical bandpass filters, wherein radiation from said illumination source passes through said filter wheel.

11. The scanner system of claim 10, wherein said filter wheel is further comprised of at least one opaque optical shutter element.

12. The scanner system of claim 1, further comprising a processor coupled to said detection system, wherein said processor creates an image of said scan area of said sample from said detection system output signals.

13. The scanner system of claim 12, further comprising a monitor coupled to said processor, wherein said image is displayed on said monitor.

14. The scanner system of claim 1, wherein said sample illumination source further comprises an external source port allowing an external source to be coupled to said scanner system, wherein radiation from said external source passes through said external source port and said scan head to said portion of said sample.

15. The scanner system of claim 14, further comprising said external source coupled to said external source port, wherein said external source is selected from the group consisting of lasers and broadband sources.

16. The scanner system of claim 14, further comprising:
   a radiation collimating system, wherein radiation from said external source passes through said collimating system; and
   a translation stage system coupled to said collimating system, said translation stage system allowing said external source radiation to be optimally coupled to said scanner system.

17. The scanner system of claim 16, further comprising a processor coupled to said translation stage system, said processor controlling movement of said translation stage system and optimization of said coupling of said external source radiation to said scanner system.

18. The scanner system of claim 17, wherein said coupling optimization is determined by peaking said output signal from said detection system during movement of said translation stage system.

19. The scanner system of claim 17, wherein said coupling optimization is determined by peaking a signal from an alignment detector during movement of said translation stage system.

20. The scanner system of claim 15, wherein radiation from said external source and said laser simultaneously illuminate said sample.

21. The scanner system of claim 1, wherein said radiation emitted by said sample is scattered radiation originating with said illumination source.

22. The scanner system of claim 1, wherein said radiation emitted by said sample is due to fluorescence, wherein said fluorescence is of a wavelength distinguishable from said first and second wavelengths of said illumination source.

23. The scanner system of claim 1, wherein said sample is selected from the group consisting of fluorescent samples, storage phosphor screens, samples containing DNA stains, samples containing chemiluminescent probes, and samples containing protein dyes.

24. The scanner system of claim 1, wherein said sample is selected from a group of sample types consisting of gels, membranes, TLC plates, sequencing plates, DNA hybridization arrays, and PCR chips.

25. The scanner system of claim 1, wherein said first illumination source wavelength is suitable for use with storage phosphor screens based on BaFBr:Eu and said second illumination source wavelength is suitable for use with storage phosphor screens based on SrS:Ce and SrS:Sm.

26. The scanner system of claim 2, further comprising a first optical encoder coupled to said first translation stage and a second optical encoder coupled to said second translation stage, wherein said first and second optical encoders provide absolute position information for said scan head.

27. The scanner system of claim 1, wherein said illumination source is modulated and said detection system is modulated.

28. The scanner system of claim 27, further comprising a processor coupled to said modulated detection system, wherein said illumination source excites fluorescence in said sample, and wherein said processor determines fluorescence lifetimes from said output signals of said modulated detection system.

29. A storage phosphor screen scanner, comprising:
a laser source simultaneously emitting radiation at a first wavelength and a second wavelength, wherein said first wavelength is compatible with BaFBr:Eu storage phosphor screens and said second wavelength is compatible with SrS:Ce and SrS:Sm storage phosphor screens;
a screen scanning head coupled to said laser source by at least one excitation optical fiber, wherein said scanning head is coupled to an x-y scanning system;
a detection system comprised of a first detector monitoring radiation of a third wavelength and a second detector monitoring radiation of a fourth wavelength and a beam splitter transmitting radiation of said third wavelength to said first detector and reflecting radiation of said fourth wavelength to said second detector, wherein said first and second detectors simultaneously monitor radiation, and wherein said detection system is coupled to said scanning head by at least one collection optical fiber; and
a processor coupled to said x–y scanning system, said processor controlling an area of a sample scanned by said scanning head.

30. The storage phosphor screen scanner of claim 29, wherein said processor controls a resolution and a scan speed associated with said x-y scanning system.

31. The storage phosphor screen scanner of claim 29, wherein said first wavelength is approximately 532 nanometers and said second wavelength is approximately 1064 nanometers.

32. The storage phosphor screen scanner of claim 29, further comprising an external source coupled to said scanning head through said at least one excitation optical fiber, wherein said external source emits radiation of a fifth wavelength distinguishable from said first and second wavelengths.

33. The storage phosphor screen scanner of claim 29, further comprising a sample storage phosphor screen, said sample storage phosphor screen exposed in a substantially light tight exposure box prior to insertion into said storage phosphor screen scanner.

34. The storage phosphor screen scanner of claim 29, further comprising a wavelength selection system interposed between said laser and said at least one excitation optical fiber.

35. The storage phosphor screen scanner of claim 29, further comprising a wavelength selection system interposed between said at least one collection optical fiber and said first and second detectors.

36. The storage phosphor screen scanner of claim 29, wherein said processor is coupled to said detection system, and wherein said processor creates an image of a sample within said storage phosphor screen scanner.

37. A scanner system, comprising:
a sample illumination source, said illumination source comprising:
an internal source emitting radiation of at least a first wavelength; and
an external source emitting radiation of at least a second wavelength;
a radiation collimating system, wherein radiation from said external source passes through said collimating system;
a translation stare system coupled to said collimating system, said translation stage system allowing said external source radiation to be optimally coupled to said scanner system;
a processor coupled to said translation stage system, said processor controlling movement of said translation stage system and optimization of said coupling of said external source radiation to said scanner system;
a scan head for scanning an area of a sample held within a sample support, wherein said scanning is along a first direction and a second direction, wherein said scan head simultaneously directs said radiation of said at least first and second wavelengths from said sample illumination source to a portion of said sample;
a detection system for monitoring radiation emitted by said sample, wherein said detection system outputs a signal corresponding to the intensity of said monitored radiation; and a wavelength selection system coupled to said detection system, wherein said wavelength selection system controls the wavelength of radiation monitored by said detection system.

38. The scanner system of claim 37, further comprising:
a first translation stage for moving said scan head in said first direction;
a second translation stage for moving said scan head in said second direction; and
a processor coupled to said first and second translation stages, said processor controlling movement of said scan head.

39. The scanner system of claim 38, further comprising a third translation stage coupled to said scan head, said third translation stage controlling motion of said scan head in a third direction, wherein said third direction is perpendicular to a plane formed by said first and second directions, and wherein said processor controls movement of said third translation stage.

40. The scanner system of claim 37, wherein said detection system is further comprised of a first detector and a second detector, and wherein said scanner system further comprises a beam splitter, wherein said beam splitter allows said first detector and said second detector to simultaneously monitor radiation emitted by said sample, wherein said first detector monitors radiation of a third wavelength and said second detector monitors radiation of a fourth wavelength.

41. The scanner system of claim 40, wherein said first and second detectors are photomultiplier tube detectors.

42. The scanner system of claim 37, wherein a first intensity of said internal source emissions is approximately equal to a second intensity of said external source emissions.

43. The scanner system of claim 37, further comprising a bifurcated bundle of optical fibers having distal and proximal ends, said optical fibers comprising at least one emitter fiber and at least one collecting fiber, said distal ends of said at least one emitter fiber and said at least one collecting fiber coupled to said scan head, wherein said radiation from said sample illumination source is focussed by a first focussing optic into said proximal end of said at least one emitter fiber, said radiation passing through said at least one emitter fiber and being focussed by a second focussing optic onto said portion of said sample, and wherein said radiation emitted by said portion of said sample is collected by a collection optic and focussed onto said distal end of said at least one collecting fiber, and wherein said proximal end of said at least one collecting fiber is positioned to pass said collected radiation to said detection system through said wavelength selection system.

44. The scanner system of claim 37, further comprising a processor coupled to said detection system, wherein said processor creates an image of said scan area of said sample from said detection system output signals.

45. The scanner system of claim 38, further comprising a first optical encoder coupled to said first translation stage and a second optical encoder coupled to said second translation stage, wherein said first and second optical encoders provide position information for said scan head.

* * * * *